(12) United States Patent
Godfrey et al.

(10) Patent No.: US 7,220,382 B2
(45) Date of Patent: May 22, 2007

(54) USE OF DISULFONATED ANTHRACENES AS INERT FLUORESCENT TRACERS

(75) Inventors: Martin R. Godfrey, Naperville, IL (US); John E. Hoots, St. Charles, IL (US)

(73) Assignee: Nalco Company, Naperville, IL (US)

( * ) Notice: Subject to any disclaimer, the term of this patent is extended or adjusted under 35 U.S.C. 154(b) by 3 days.

(21) Appl. No.: 10/631,606

(22) Filed: Jul. 31, 2003

(65) Prior Publication Data

US 2005/0025659 A1    Feb. 3, 2005

(51) Int. Cl.
*A61L 2/24* (2006.01)

(52) U.S. Cl. .......................... 422/3; 210/709; 210/739; 210/749; 422/7; 422/14; 422/119

(58) Field of Classification Search .................... 422/3, 422/7, 14, 82.08, 119; 210/709, 739, 749
See application file for complete search history.

(56) References Cited

U.S. PATENT DOCUMENTS

| | | | |
|---|---|---|---|
| 4,783,314 A | 11/1988 | Hoots et al. | |
| 4,992,380 A | 2/1991 | Moriarty et al. | |
| 5,006,311 A | 4/1991 | Hoots et al. | |
| 5,041,386 A | 8/1991 | Pierce et al. | |
| 5,171,450 A | 12/1992 | Hoots | |
| 5,278,074 A | 1/1994 | Rao et al. | |
| 5,282,379 A | 2/1994 | Harder et al. | |
| 5,304,800 A | 4/1994 | Hoots et al. | |
| 5,320,967 A | 6/1994 | Avallone et al. | |
| 5,416,323 A | 5/1995 | Hoots et al. | |
| 5,503,775 A | 4/1996 | Rao et al. | |
| 5,736,405 A | 4/1998 | Alfano et al. | |
| 6,255,118 B1 | 7/2001 | Alfano et al. | |
| 6,315,909 B1 | 11/2001 | Hoots et al. | |
| 6,336,058 B1 | 1/2002 | Fowee | |
| 6,369,894 B1 | 4/2002 | Rasimas et al. | |
| 6,436,711 B1 | 8/2002 | Davis et al. | |
| 6,556,027 B2 | 4/2003 | Banks | |
| 6,566,139 B2 | 5/2003 | Davis et al. | |
| 6,587,753 B2 | 7/2003 | Fowee | |
| 6,730,227 B2 * | 5/2004 | Zeiher et al. | ................ 210/650 |
| 6,838,001 B2 * | 1/2005 | Zeiher et al. | ................ 210/639 |

OTHER PUBLICATIONS

Morley, J.O., "Studies on the sulfonation of anthracene. Part 1. Sulfonation in neutral or basic solvents.", Journal of the Chemical Society, Perkin Transactions 2, pp. 1554-1559, 2003.

Morley, J.O., "Studies on the sulfonation of anthracene. Part 2. Sulfonation in acetic acid and related solvents.", Journal of the Chemical Society, Perkin Transactions 2, pp. 1560-1564, 2003.

* cited by examiner

*Primary Examiner*—Krisanne Jastrzab
(74) *Attorney, Agent, or Firm*—Peter A. DiMattia; Thomas M. Breininger

(57) ABSTRACT

The use of an isomer of anthracene disulfonic acid as an inert fluorescent tracer is described and claimed. The utility of this type of inert fluorescent tracer in boiler systems to trace unwanted carryover of boiler water into a steam line is also described and claimed.

1 Claim, No Drawings

USE OF DISULFONATED ANTHRACENES AS INERT FLUORESCENT TRACERS

FIELD OF INVENTION

This invention is in the field of industrial water systems. Specifically, this invention is in the field of the use of inert fluorescent tracers in the water of an industrial water system.

BACKGROUND OF THE INVENTION

Industrial water systems exist so that necessary chemical, mechanical and biological processes can be conducted to achieve the desired outcome of the process. The use of inert fluorescent tracers in industrial water systems is well-known in the art; see U.S. Pat. No. 4,783,314 Fluorescent Tracers-Chemical Treatment Monitors. In this patent, the fluorescent signal of the inert fluorescent tracer is used to determine how much inert fluorescent tracer is present, and by knowing the amount of inert fluorescent tracer that is present it is possible to determine the amount of treatment product that is present in the industrial water system. If the amount of treatment product that is present is not what is desired then the feed rate of treatment product or other operating parameters of the industrial water system can be adjusted to provide the desired amount of treatment product.

Inert fluorescent tracers are used in boilers; see U.S. Pat. No. 5,041,386 Concentration Cycles, Percent life Holding Time and Continuous Treatment Concentration Monitoring in Boiler Systems by Inert Tracers.

Inert tracers are required in order to conduct the methods described and claimed in these and other patents. Known fluorescent tracers, such as 1,5-naphthalenedisulfonic acid, disodium salt and 1,3,6,8-pyrenetetrasulfonic acid, tetrasodium salt are commercially available from Ondeo Nalco Company, Ondeo Nalco Center, 1601 W. Diehl Road, Naperville Ill. 60563, (630) 305-1000.

Inert tracers are typically defined as those tracers that have a detectable fluorescent signal that does not change more than 10% in the presence of water and the other ingredients in the water of an industrial water system. While water is obviously the major component of an industrial water system there are typically other materials present in an industrial water system. These can include anything from innocuous materials all the way to highly reactive, oxidizing biocides. It is difficult therefore, to identify and use inert tracers for all known industrial water systems. Thus, it is always desirable to identify, test and confirm the use of new materials as inert fluorescent tracers.

SUMMARY OF THE INVENTION

The first aspect of the instant claimed invention is in a method of using an inert fluorescent tracer in an industrial water system comprising the steps of:

1) providing an industrial water system;
2) adding to the water of said industrial water system a treatment chemical wherein said treatment chemical includes an inert fluorescent tracer in a known proportion;
3) providing a fluorometer capable of detecting the fluorescent signal of said inert fluorescent tracer;
4) using said fluorometer to detect and measure the fluorescent signal of said inert fluorescent tracer in the water of said industrial water system;
5) using the detected and measured fluorescent signal of said inert fluorescent tracer to determine how much of the treatment chemical is present in the water of said industrial water system and optionally;
6) adjusting the operating parameters of said industrial water system such that the amount of treatment chemical present is optimal for the operating conditions of said industrial water system; the improvement comprising using as the inert fluorescent tracer an isomer of anthracene disulfonic acid or any of its known salts.

The second aspect of the instant claimed invention is a method of tracing the water in a boiler and a boiler water system, comprising the steps of:

(a) providing a boiler and a boiler water system;
(b) placing in the water of said boiler, an inert fluorescent tracer which has a detectable fluorescent signal;
(c) providing a fluorometer capable of detecting the fluorescent signal of said inert fluorescent tracer;
(d) using said fluorometer to detect and measure the fluorescent signal of said inert fluorescent tracer in the water of said boiler;
(e) using said fluorometer to detect and measure the fluorescent signal of said inert fluorescent tracer in fluid removed from a steam line of said boiler;
(f) using the detected fluorescent signal of said inert fluorescent tracer in the water of said boiler and in fluid removed from a steam line of said boiler to determine the amount of unwanted carryover of boiler water into a steam line; and optionally
(g) adjusting the operating parameters of said boiler to minimize the amount of unwanted carryover of boiler water into a steam line.

DETAILED DESCRIPTION OF THE INVENTION

Throughout this patent application the following terms have the indicated definitions: "CAS #" refers to the Chemical Abstracts Services Registry Number.

Nalco refers to Ondeo Nalco Company, Ondeo Nalco Center, 1601 W. Diehl Road, Naperville Ill. 60563, telephone number (630) 305-1000.

The first aspect of the instant claimed invention is in a method of using an inert fluorescent tracer in an industrial water system comprising the steps of:

1) providing an industrial water system;
2) adding to the water of said industrial water system a treatment chemical wherein said treatment chemical includes an inert fluorescent tracer in a known proportion;
3) providing a fluorometer capable of detecting the fluorescent signal of said inert fluorescent tracer;
4) using said fluorometer to detect and measure the fluorescent signal of said inert fluorescent tracer in the water of said industrial water system;
5) using the detected and measured fluorescent signal of said inert fluorescent tracer to determine how much of the treatment chemical is present in the water of said industrial water system; and optionally;
6) adjusting the operating parameters of said industrial water system such that the amount of treatment chemical present is optimal for the operating conditions of said industrial water system; the improvement comprising using as the inert fluorescent tracer an isomer of anthracene disulfonic acid or any of its known salts.

Industrial water systems include the following: cooling water systems, including open recirculating, closed and once-through cooling water systems; boilers and boiler water systems; petroleum wells, downhole formations, geothermal wells and other oil field applications; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

Treatment chemicals for use in industrial water systems include commercially available corrosion inhibitors, biological control agents, scale inhibitors, dispersants, coagulants, flocculants, and pH control agents. These commercially available products are well known to people in the art of industrial water chemistry.

Known isomers of anthracene disulfonic acid, and certain of their known salt forms include the following:

CAS # 13189-75-8 1,5-anthracene disulfonic acid, disodium salt;
CAS # 55750-36-2 1,8-anthracene disulfonic acid disodium salt;
CAS # 61736-91-2 1,5-anthracene disulfonic acid;
CAS # 61736-92-3 1,8-anthracene disulfonic acid;
CAS # 61736-67-2 1,5-anthracene disulfonic acid, magnesium salt;
CAS # 61736-93-4 1,6-anthracene disulfonic acid;
CAS # 61736-94-6 1,7-anthracene disulfonic acid;
CAS# 61736-95-6 2,6-anthracene disulfonic acid; and
CAS# 61736-96-7 2,7-anthracene disulfonic acid.

The preferred isomers of anthracene disulfonic acid are 1,5-anthracene disulfonic acid, magnesium salt, 1,5-anthracene disulfonic acid, disodium salt and 1,8-anthracene disulfonic acid disodium salt and mixtures thereof. The most preferred isomer of anthracene disulfonic acid is about a 2:1 mixture of 1,5-anthracene disulfonic acid, disodium salt and 1,8-anthracene disulfonic acid disodium salt.

The primary utility of these isomers of anthracene disulfonic acid is the fact that the wavelength of light that excites the isomers, 365 nm, is about the midpoint of the wavelength of light supplied by a commercially available UV LED fluorometer, such as a TRASAR® 3000 or TRASAR® 8000 fluorometer. Also, another useful feature of these isomers is that the primary wavelength of light that excites them, 365 nm, is sufficiently different from their emission wavelength 400-430, that it is easy to know when the fluorometer detects a fluorescent signal from these isomers.

Isomers of anthracene disulfonic acid can be obtained by following synthetic techniques known in the art of organic chemistry. See GB 1214256, A method of preparing anthraquinone 1,5-disulphonic acid, published Oct. 13, 1976, assigned to Imperial Chemical Industries, Studies on the Sulfonation of Anthracene. Part 1. Sulfonation in neutral or basic solvents, by John O. Morley, Journal of the Chemical Society, Perkin Transactions 2: Physical Organic Chemistry (1972-1999) (1976), (13), 1554-9, Studies on the Sulfonation of Anthracene. Part 2. Sulfonation in acetic acid and related solvents, by John O. Morley, Journal of the Chemical Society, Perkin Transactions 2: Physical Organic Chemistry (1972-1999) (1976), (13), 1560-4.

Fluorometers suitable for use in the instant claimed invention are commercially available from Nalco, TRASAR® 8000, TRASAR® 3000, TRASAR® Xe-2 fluorometer, TRASAR® 350. Other suitable fluorometers are available from Spex. The preferred fluorometers are a TRASAR® 3000 unit and a TRASAR® Xe-2 fluorometer.

How to set up and program a fluorometer and use it to measure the fluorescent signal of a fluorescent tracer is known to people of ordinary skill in the art of fluorometry. The information known about the fluorescent properties of anthracene disulfonic acid and what fluorometer is appropriate to use with each isomer appears in the following information.

|   | Fluorometer | Light source | Detector | Compound | Excitation wavelength (nm) | Emission wavelength (nm) | Lower detection limit | Upper detection limit |
|---|---|---|---|---|---|---|---|---|
| 1) | TRASAR® 8000 handheld | UV LED | pd | Mg 1,5 ADSA | 365 | 400 | 0.1 ppm | 2 ppm |
| 2) | TRASAR® 3000 on line | UV LED | pd | Mg 1,5 ADSA | 365 | 400 | 0.1 ppm | 10 ppm |
| 3) | Modified TRASAR® 3000 | UV LED | pd | Na2 1,5 ADSA, Na2 1,8 ADSA mixture | 365 | 430 | 6.7 ppb | 13 ppm |
| 4) | Xe-2 fluorometer | Xe flashlamp | pd | Na2 1,5 ADSA, Na2 1,8 ADSA mixture | 365 | 430 | 1.75 ppb | 11 ppm |
| 5) | Xe-2 fluorometer | Xe flashlamp | pd | Na2 1,5 ADSA, Na2 1,8 ADSA mixture | 254 | 430 | 0.45 ppb | >1 ppm |
| 6) | TRASAR® 350 | Hg emission lamp | pmt | Mg 1,5 ADSA | 365 | 415 | 1 ppb | |
| 7) | TRASAR® 350 | Hg emission lamp | pmt | Mg 1,5 ADSA | 254 | 415 | 0.2 ppb | |

All concentrations are as active anthracene disulfonic acid
pd means photodiode, pmt means photomultiplier
1,5-anthracene disulfonic acid, magnesium salt is abbreviated Mg 1,5 ADSA.
1,5-anthracene disulfonic acid, disodium salt is abbreviated Na2 1,5 ADSA and
1,8-anthracene disulfonic acid, disodium salt is abbreviated Na2 1,8 ADSA After the fluorescent signal of the tracer is detected and measured, it is known how to correlate that information with the concentration of the inert fluorescent tracer and once the concentration of the inert fluorescent tracer is known that information can be used to determine the amount of treatment chemical present and that information can be used to optimize the performance of the industrial water system by adjusting the amount of treatment chemical present.

The second aspect of the instant claimed invention is a method of tracing the water in a boiler and a boiler water system, comprising the steps of:

(a) providing a boiler and a boiler water system;
(b) placing in the water of said boiler, an inert fluorescent tracer which has a detectable fluorescent signal;
(c) providing a fluorometer capable of detecting the fluorescent signal of said inert fluorescent tracer;
(d) using said fluorometer to detect and measure the fluorescent signal of said fluorescent tracer in the water of said boiler;
(e) using said fluorometer to detect and measure the fluorescent signal of said fluorescent tracer in fluid removed from a steam line of said boiler;
(f) using the detected fluorescent signal of said inert fluorescent tracer in the water of said boiler and in fluid removed from a steam line of said boiler to determine the amount of unwanted carryover of boiler water into a steam line; and optionally
(g) adjusting the operating parameters of said boiler to minimize the amount of unwanted carryover of boiler water into a steam line.

Isomers of anthracene disulfonic acid, and certain of their known salt forms suitable for use in this method include the following: 1,5-anthracene disulfonic acid, disodium salt; 1,8-anthracene disulfonic acid disodium salt; 1,5-anthracene disulfonic acid; 1,8-anthracene disulfonic acid; 1,5-anthracene disulfonic acid, magnesium salt; 1,6 anthracene disulfonic acid; 1,7 anthracene disulfonic acid; 2,6-anthracene disulfonic acid and 2,7-anthracene disulfonic acid. The preferred isomers and salts of anthracene disulfonic acid are 1,5-anthracene disulfonic acid, magnesium salt, 1,5-anthracene disulfonic acid, disodium salt and 1,8-anthracene disulfonic acid disodium salt and mixtures thereof. The most preferred anthracene disulfonic acid tracer is a 2:1 mixture of 1,5-anthracene disulfonic acid, disodium salt and 1,8-anthracene disulfonic acid, disodium salt.

In this method, the amount of isomer of anthracenedisulfonic acid or a known salt of anthracenedisulfonic acid added to the water in the boiler is from about 0.0001 ppm to about 10,000 ppm, preferably from about 0.005 ppm to about 10 ppm and most preferably from about 0.01 ppm to about 1.0 ppm.

The fluorometers that can be used in the second aspect of the instant claimed invention are the same as those fluorometers that can be used in the first aspect of the instant claimed invention.

How to set up and program a fluorometer and use it to measure the fluorescent signal of a Fluorescent Tracer is known to people of ordinary skill in the art of fluorometry. After the fluorescent signal of the tracer is detected and measured, it is known how to correlate that information with the concentration of the inert fluorescent tracer and once the concentration of the inert fluorescent tracer is known that information can be used to determine the amount of carryover of boiler water present in a steam line of the boiler and that information can then be used to optimize the operation of the boiler.

The fluorometer is used to detect and measure the fluorescent signal of fluid removed from a steam line. If the inert fluorescent tracer is present in the boiler water and there is carryover of boiler water into a steam line, this undesired carryover can be detected and quantified by measuring the fluorescent signal in the fluid removed from the steam line.

To further elaborate, the wide detection range of the inert fluorescent isomers of anthracene disulfonic acid provides unique capabilities for the detection of mechanical carryover in boiler systems. Mechanical carryover is a term used to describe the entrainment of droplets of boiler water in the steam exiting the boiler. The droplets carry with them everything that is dissolved in the boiler water including salts such as NaOH. When an inert tracer, such as an isomer of anthracene disulfonic acid or one of its salt forms, is present, it too will be part of the water carried over. Mechanical carryover adversely affects steam purity and some components, present in the carryover, such as NaOH, can severely damage valuable equipment that uses the steam including electric generation or drive turbines. Since mechanical carryover can damage valuable equipment and cause extremely expensive unplanned outages of such equipment it is desirable to monitor the carryover process on-line or with grab sample analysis. The use of an inert fluorescent tracer can facilitate this process. However, for all known inert fluorescent tracers, long-term, continuous carryover monitoring is impractical because the tracer must be present in the boiler water at concentrations far above what are considered "normal use" levels. The extremely wide detection range for isomers of anthracene disulfonic acid and the various salts thereof, makes continuous monitoring of mechanical carryover in boiler systems readily achievable.

Therefore, if the fluorescent signal of the inert tracer is found in the fluid removed from a steam line it is indicative of the amount of carryover occurring and the operating conditions of the boiler can be adjusted to reduce the amount of carryover.

The following examples are presented to be illustrative of the present invention and to teach one of ordinary skill how to make and use the invention. These examples are not intended to limit the invention or its protection in any way.

EXAMPLES

Example 1

Sample Preparation:

Fluorescent tracer solutions (see Table 1) were prepared by adding a specified weighed amount of a stock solution of fluorescent tracer into a 250 mL polypropylene bottle. The samples were stored at ambient temperature for a total of 59 days. Test samples were taken at defined intervals from each traced liquid solution (initial, 4 days and 59 days) and the fluorescence signals of each sample were measured.

TABLE 1

| Fluorescent Tracer | Stock Solution Concentration* | Amount Added | Test Solution Concentration |
|---|---|---|---|
| 1,5-naphthalenedisulfonic acid, disodium salt** | 130 ppm | 0.31 gram | 0.4 ppm |
| 1,3,6,8-pyrenetetrasulfonic acid, tetrasodium salt** | 10 ppm | 1.00 gram | 0.1 ppm |
| fluorescein, monopotassium salt** | 0.3 ppm | 3.33 gram | 0.010 ppm |

TABLE 1-continued

| Fluorescent Tracer | Stock Solution Concentration* | Amount Added | Test Solution Concentration |
|---|---|---|---|
| 1,5-anthracenedisulfonic acid, magnesium salt | 109 ppm | 0.74 gram | 0.8 ppm |

**comparative examples are not examples of the instant claimed invention.
*Tracer concentration expressed as acid equivalent form Fluorometer Selection and Set-Up for Detection of Fluorescent Signal A SPEX fluorometer (Model FluoroMax-2) was used to measure fluorescent signals and determine dosages of fluorescent tracers being tested. The fluorescent signal of each tracer was measured at the excitation and emission wavelengths listed in Table 2. A rectangular quartz cuvette (10 mm×3 mm, inner dimensions) was used to hold the sample. Each combination of fluorescent tracer was normalized to 100% in the "initial sample" (Table 3) which was measured within one hour after the tracer and corrosive liquid were mixed. The fluorescence of the tracer and water solutions were tested again at 4 days and 59 elapsed time. The relative fluorescent signals of the samples measured at 4 days and 59 days are listed in Table 3. The fluorescent signals which change by less than or equal to +/−10% (% relative fluorescence range=90 to 110%, as compared to initial sample) on Day 59 are given an acceptable rating and are defined as being inert over long time periods in the liquid environment being tested.

TABLE 2

| Fluorescent Tracer | Excitation Wavelength (nm) | Emission Wavelength (nm) |
|---|---|---|
| 1,5-naphthalenedisulfonic acid, disodium salt* | 290 nm | 330 nm |
| 1,3,6,8-pyrenetetrasulfonic acid, tetrasodium salt* | 365 nm | 400 nm |
| fluorescein, monopotassium salt* | 486 nm | 515 nm |
| 1,5-anthracenedisulfonic acid, magnesium salt | 365 nm | 415 nm |

*comparative example, not an example of this invention

TABLE 3

Relative Fluorescence over Time of Fluorescent Tracer

| | | % Relative Fluorescence | | | |
|---|---|---|---|---|---|
| Sample # | Fluid Tested | Initial | 4 days | 59 days | Acceptable ? |
| 1,5-naphthalenedisulfonic acid, disodium salt (not an example of this invention) | | | | | |
| 1 | Water | 100 | 100 | 100 | yes |
| 1,3,6,8-pyrenetetrasulfonic acid, tetrasodium salt (not an example of this invention) | | | | | |
| 8 | Water | 100 | 100 | 100 | yes |
| fluorescein, monopotassium salt (not an example of this invention) This sample was kept in the dark to avoid light degradation of the fluorescein molecule | | | | | |
| 15 | Water | 100 | 100 | 100 | yes |
| 1,5-anthracenedisulfonic acid, magnesium salt (an example of this invention) | | | | | |
| 22 | Water | 100 | 100 | 100 | yes |

Thus, 1,5-anthracenedisulfonic acid, magnesium salt, is a suitable inert fluorescent tracer in room temperature water for at least 59 days.

Example 2

A sample of 1,5-anthracene disulfonic acid disodium salt (hereinafter 1,5-ADSA) prepared by reduction of the anthraquinone was tested for thermal stability in the simulation boilers.

Scale boiler test #17824 was run with 0.1 ppm of both 1,5 naphthalene disulfonic acid, disodium salt (hereinafter NDSA) and 0.1 ppm of 1,5-ADSA in the feedwater. The feedwater also contained 26 ppm of NaCl and was adjusted to pH=10 with NaOH. The boiler was run at 10 cycles of concentration and allowed to come to a steady state at four different pressures 1000 psig, 1500 psig, 1800 psig and 2100 psig. Blowdown samples were diluted 10 fold and analyzed for the fluorescent signals of both NDSA and 1,5-ADSA by a fluorometer. The fluorescent signal of NDSA was recorded at 290 nm excitation and 330 nm emission. The fluorescence signal of 1,5-ADSA was recorded at 365 nm excitation and 410 nm emission. The ratio of the fluorescence intensity of the two tracers in each blowdown sample was compared to the average ratio measured in samples taken from the deaerator drop leg because it is known that fluorescent tracers are typically stable under the conditions found in the deaerator (110° C. and 5 psig). In this way the recovery of the 1,5-ADSA could be measured using NDSA as an internal standard.

This recovery percentage is only relative since we know that NDSA, a tracer currently being used in boilers, can suffer some decomposition at the highest pressure measured in this test. The results are given in Table Example 2. The estimated error in the measurements is +/−5%.

TABLE EXAMPLE 2

1,5-Anthracene disulfonic acid recovery

| Boiler Pressure | 1,5-ADSA Recovery |
|---|---|
| 1000 psig | 93% |
| 1500 psig | 92% |
| 1800 psig | 96% |
| 2100 psig | 87% |

The results indicate that the fluorescent signal of 1,5-ADSA is acceptably inert (+/−10%) to 1800 psig. Above 1800 psig, the fluorescent signal of 1,5-ADSA suffers some decomposition.

Example 3

An oxygen scavenger product, carbohydrazide in water, available as Eliminox®, from Nalco, containing a 1.75% mixture (about 2:1 of the 1,5-anthracene disulfonic acid, disodium salt and 1,8-anthracene disulfonic acid, disodium salt, calculated as just the "acid active" component) of inert fluorescent tracer is injected into the feedwater system of a boiler. In this boiler, the feedwater concentration is being controlled manually. Normal use concentrations for boiler treatments fall in the 0.5-100 ppm range. In this case, the Eliminox® oxygen scavenger is fed at a concentration of 1.25 ppm that delivers a concentration of 22 ppb as acid active anthracene disulfonic acid to the feedwater.

Since salts, including the tracer concentrate in the boiler water because relatively pure water is removed as steam the concentration of tracer in the boiler water will be higher than in the feedwater. Boiler cycles of concentration is a term that reflects this concentration mechanism and is the factor which feedwater concentrations can be multiplied by to arrive at boiler water concentrations. Boiler cycles can range from 5-200.

In this example, the boiler is operating at 50 cycles of concentration so that the boiler water concentration of tracer as anthracene disulfonic acid is 1.1 ppm. The pressure in the boiler is maintained at about 1000 psig. A representative sample of fluid is obtained from the saturated steam line exiting the boiler using an isokinetic nozzle aligned in the steam line, parallel with the flow of direction of the steam. This setup for the nozzle ensures that the fluid sample is representative rather than just being comprised of one or more fractions of the fluid stream. The fluid sample removed is fully condensed and conditioned to an appropriate temperature and pressure then passed through the optical cell of an on-line fluorometer. The fluorometer is an Xe-2 fluorometer fitted with an excitation filter set at 254 nm and an emission filter set at 430 nm which is a setup capable of detecting 0.45 ppb of anthracene disulfonic acid with high certainty.

Using the detected fluorescent signal it is possible to detect carryover at a level as low as 0.04%. Adjustments to boiler operating parameters such as drum level and blowdown rate are made in response to carryover greater than 0.04%. Carryover limits of no more than 0.03% to 0.08% are specified for most boilers operating up to 1000 psig. When a lower carryover limit is required, then more of the inert fluorescent tracer is required in order for it to be functional to be used to detect carryover at the lower level.

The present method has been described in an illustrative manner. Many modifications and variations are possible in light of the above teachings. It is, therefore, to be understood that within the scope of the appended claims the invention may be practiced otherwise than as specifically described.

What is claimed is:

1. A method of tracing the water in a boiler and a boiler water system, comprising the steps of:
   a) providing a boiler and a boiler water system;
   b) placing in the water of said boiler, an inert fluorescent tracer which has a detectable fluorescent signal, wherein said inert fluorescent tracer is an isomer of anthracene disulfonic acid or a salt thereof;
   c) providing a fluorometer capable of detecting the fluorescent signal of said inert fluorescent tracer;
   d) using said fluorometer to detect and measure the fluorescent signal of said inert fluorescent tracer in the water of said boiler;
   e) using said fluorometer to detect and measure the fluorescent signal of said inert fluorescent tracer in fluid removed from a steam line of said boiler;
   f) using the detected fluorescent signal of said inert fluorescent tracer in the water of said boiler and in fluid removed from a steam line of said boiler to determine the amount of unwanted carryover of boiler water into a steam line; and optionally
   g) adjusting the operating parameters of said boiler to minimize the amount of unwanted carryover of boiler water into a steam line.

* * * * *